US00PP12198P2

(12) United States Plant Patent
Heffner

(10) Patent No.: US PP12,198 P2
(45) Date of Patent: Nov. 13, 2001

(54) *SAGITTARIA AUSTRALIS* 'BENNI'

(75) Inventor: Randolph A. Heffner, Pipersville, PA (US)

(73) Assignee: Aquascapes Unlimited, Inc., Pipersville, PA (US)

( * ) Notice: Subject to any disclaimer, the term of this patent is extended or adjusted under 35 U.S.C. 154(b) by 0 days.

(21) Appl. No.: 09/474,055

(22) Filed: Dec. 28, 1999

(51) Int. Cl.[7] ..... A01H 5/00

(52) U.S. Cl. ..... Plt./342
(58) Field of Search ..... Plt./342

*Primary Examiner*—Bruce R. Campell
*Assistant Examiner*—June Hwu

(57) ABSTRACT

*Sagittaria australis* 'Benni' is a new cultivar distinguished by greyed-purple leaves with green venation which are produced throughout the season, and greyed-purple bracts and sepals, which are apparent throughout the flowering season. The new plant produces a very desirable emerging aquatic plant, which is useful for decorations in ponds. The plant flowers from July through September.

2 Drawing Sheets

FIELD OF THE INVENTION

*Sagittaria australis* 'Benni' is a herbaceous ornamental aquatic perennial suitable for the water garden market.

DESCRIPTION OF RELEVANT PRIOR ART

The following chart summarizes some of the differences between *Sagittaria australis* 'Benni' and the plant it most closely resembles, *Sagittaria australis* (common Appalachian arrowhead) under the same cultural conditions. Color designations are compared to the 1986 edition of R.H.S. Colour Chart, first published in 1966 by The Royal Horticultural Society, London, England.

| | *Sagittaria australis* (common) | *Sagittaria australis* 'Benni' |
|---|---|---|
| Leaf color | Green 138 B | Greyed-Purple 187A and Green 138 B and 138 C |
| Venation | Green 138 B | Green 138 C |
| Bract color | Stramineous | Greyed-Purple 187A |
| Sepals | Stramineous | Greyed-Purple 187A |

A sport seedling was found growing among cultivated *Sagittatria australis* (common Appalachian arrowhead). The plant was asexually reproduced in the greenhouses of Aquascapes Unlimited, Pipersville, Pa., by way of bare tuberiferous root division of a vegetative stock plant. By subjecting clones of this plant to successive generations of vegetative propagation, it was demonstrated that the distinctive characteristics of *Sagittaria australis* 'Benni' held true from generation to generation.

SUMMARY OF THE INVENTION

This new *Sagittaria australis* cultivar was found growing among straight species of *Sagittaria australis* in my greenhouse in Pipersville, Pa. It was selected because of its greyed-purple leaves with green venation; greyed-purple bracts at the axil, from which the flower stalk arises; and greyed-purple sepals; traits that distinguish it from other cultivars of *Sagittaria australis.* These traits seem to make the plant desirable for commercial ornamental aquatic production, as the plant should be desirable as a decoration in ponds. After selection, *Sagittaria australis* 'Benni' was vegetatively reproduced from root cuttings for test purposes in my greenhouse in Pipersville, Pa. *Sagittaria australis* 'Benni' most closely resembles *Sagittaria australis* (common name Appalachian arrowhead), but differs in that *Sagittaria australis* 'Benni' has greyed-purple leaves with green venation, greyed-purple bracts, and greyed-purple sepals, whereas *Sagittaria australis* leaves and bracts are green.

BRIEF DESCRIPTION OF THE PHOTOGRAPHS

A 3 month old *Sagittaria australis* 'Benni' plant grown in the greenhouses in saturated native soil is illustrated in the accompanying color photographs.

Photograph number 1 is a side view of a group of the plants growing among ornamental graminoides outside the greenhouse in natural daylight in August, 1999.

Photograph number 2 is a top view of the same group of plants while inside the greenhouse in May, 1999. The picture was taken with flash photography.

BOTANICAL DESCRIPTION OF THE PLANT

The following is a detailed description of *Sagittaria australis* 'Benni', a herbaceous ornamental aquatic perennial suitable for the water garden market. The plant is a sport of *Sagittaria australis* (common Appalachian arrowhead).

Classification:

*Botanical.*—*Sagittaria australis* 'Benni'.
*Common name.*—Variegated Appalachian arrowhead.
*Cultivar name.*—Benni.
*Trademark applied for.*—SILK STOCKINGS.
*Form.*—Emergent aquatic herbaceous perennial.
*Height.*—Will vary depending on age and growing conditions, and may range up to 1 meter, but typically are less than 0.5 meter. The height of the plant in the photographs is approximately 16 to 18 inches.
*Growth habit.*—The leaves originate basally, typically with aerial, expanded, often sagittate blade on a petiole about as long as the water is deep. When not sagittate, such as when the plant is immature or daylight hours are decreasing, the leaves may be elliptic-ovate in shape. The emergent portion of the plant is upright and vigorous. Generally, the plant has an overall height of 50 cm and an overall width of 30 cm.

*Growth rate.*—Rooting of bare root divisions occurs in 7–10 days under intermittent mist, assuming optimum conditions of 75° F. and greater than 12 hours of light per day. The plant will flower seasonally from July through September.

*Foliage.*—The foliage has an interstitial area, which is greyed-purple 187 A and green 138 B and 138 C, and veins, which are green 138 C. The underside of the leaves are green 138 B and 138 C. The greyed-purple color will change to a lighter shade within the same color group (187 A, B, C, D) with maturity, therefore older leaves appear predominantly green 138 B or 138 C. The main portion of the leaf blade is deltoid-ovate, relatively blunt compared to other Sagittaria species, and will vary depending on the age of the plant and the growing conditions, however typically ranges from 3 cm to 13 cm long and 2.5 cm to 10 cm wide. The leaf margin is entire and the leaf surface texture is smooth. Upper and lower leaf surfaces are similar in color and texture. The leaves originate basally, typically with aerial, expanded, often sagittate blades on a five winged (in cross section) petiole about as long as the water is deep.

*Petiole.*—The diameter of the petiole will vary based on the size of the leaf, but typically ranges from 0.25 cm to 1.5 cm. The color of the petiole typically is green 138 A.

*Flowers.*—Perfect flowers are in groups of three per whorl with 5 to 12 whorls per raceme; bracts are 7 to 30 millimeters and greyed-purple in color, papery-firm, broad based and long-acuminate. The size of the flowers and flower parts will vary depending on growing conditions. The diameter of the flowers is approximately 1.5 cm. The 3 petaled white 155 C flower is about 1.5 cm long and 1.5 cm wide, with a yellow anther. The flower pedicel is green 138 C and about 7 to 23 millimeters in length. The sepals are greyed-purple 187 B. Numerous stamens protrude from the flower and are yellow 13 A. Pistils are numerous and aggregated into a subglobulose head on a large receptacle and are stramineous or light tan. The peduncle is 138 C. The flower may last 1 to 3 days before the petals whither, depending on the temperature, humidity, and other environmental conditions.

*Seeds.*—The seeds (known as achenes) are closest to color 165 A and measure 2.3 to 3.2 mm without resin ducts, usually with one wing on each face. Wings do not extend into the beak. The beak is generally 0.7 to 1.7 mm and generally curved and obliquely ascending.

*Cold hardiness.*—The plant will grow best in USDA zone 5 to 8. *Sagittaria australis* plants' natural range extends from New York to Georgia, east of the Mississippi river.

I claim:

1. A new and distinct *Sagittaria australis* plant, substantially as herein shown and described, distinguished by its greyed-purple leaves with green venation which are produced throughout the season, and greyed-purple bracts and sepals, which are apparent throughout the flowering season.

* * * * *

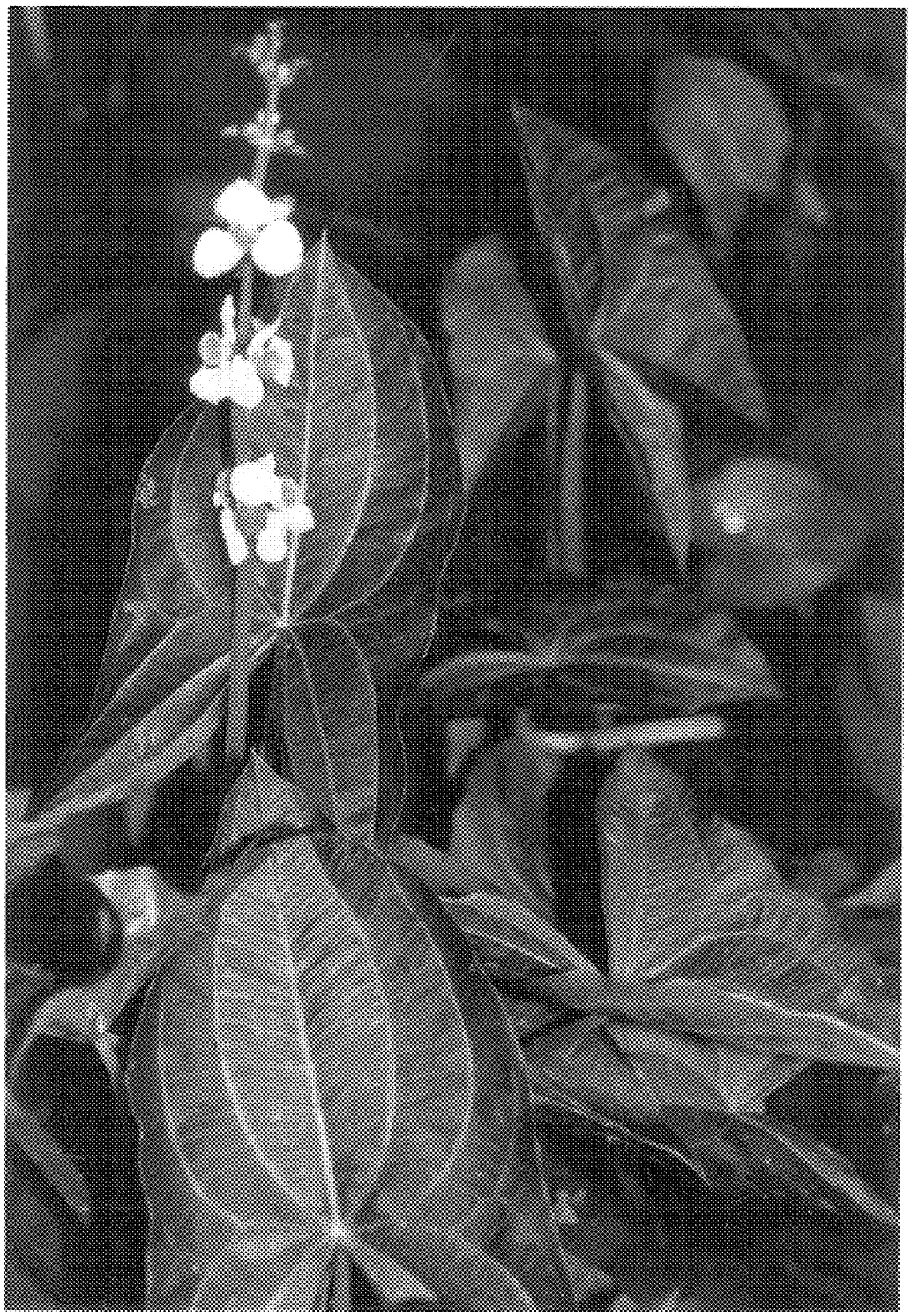
Photograph number 1

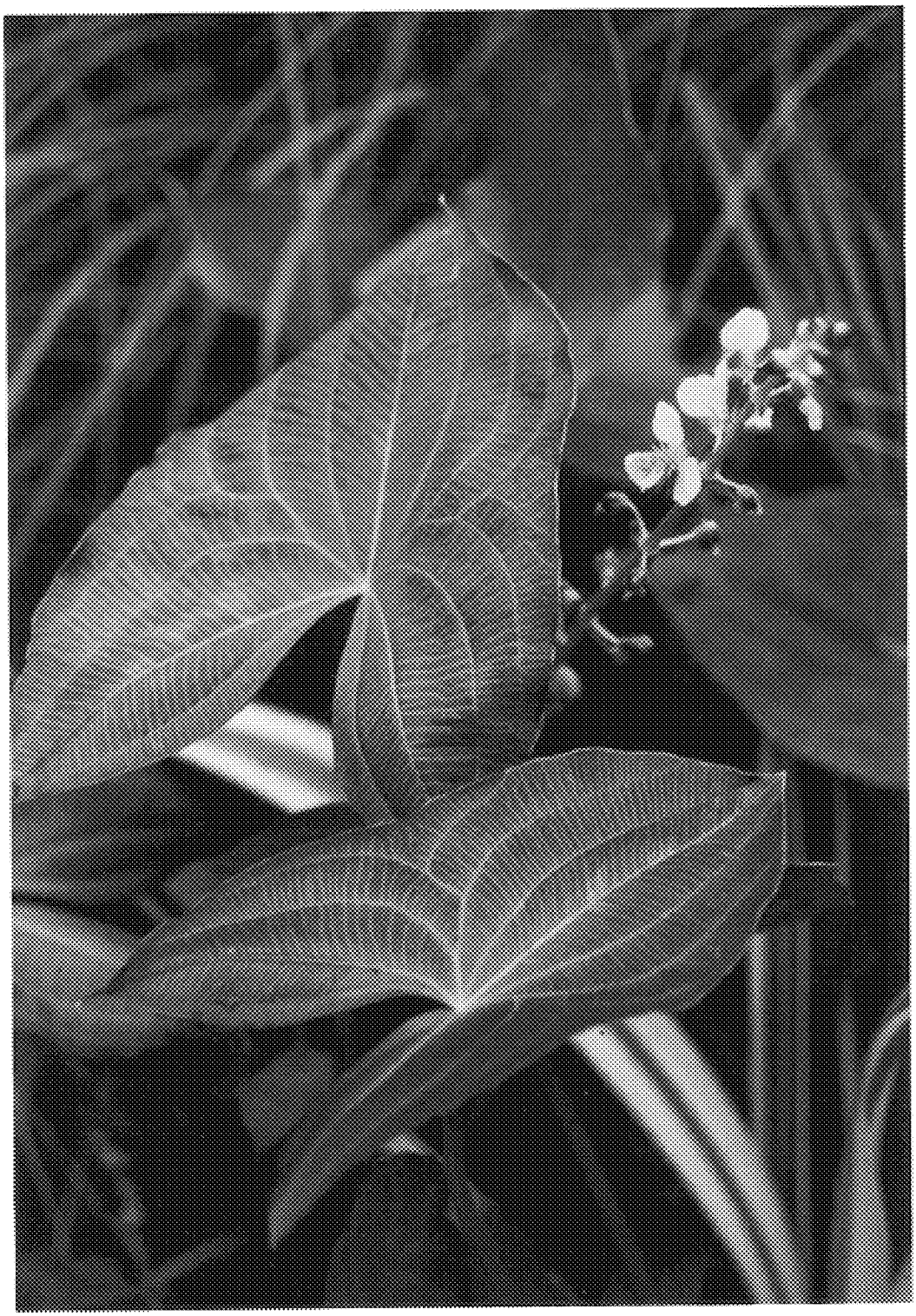
Photograph number 2